(12) United States Patent
Che et al.

(10) Patent No.: US 8,778,830 B2
(45) Date of Patent: Jul. 15, 2014

(54) SOLID SUPPORTED GOLD NANOPARTICLES, METHODS OF USE THEREOF, AND METHODS FOR MAKING SAME

(75) Inventors: Chi-Ming Che, Hong Kong (HK); Man-Ho So, Hong Kong (HK)

(73) Assignee: The University of Hong Kong, Hong Kong (HK)

( * ) Notice: Subject to any disclaimer, the term of this patent is extended or adjusted under 35 U.S.C. 154(b) by 31 days.

(21) Appl. No.: 13/107,043

(22) Filed: May 13, 2011

(65) Prior Publication Data

US 2011/0282065 A1 Nov. 17, 2011

Related U.S. Application Data

(60) Provisional application No. 61/334,804, filed on May 14, 2010.

(51) Int. Cl.
*B01J 21/00* (2006.01)
*B01J 23/02* (2006.01)
*B01J 23/04* (2006.01)

(52) U.S. Cl.
USPC ............................. 502/243; 502/344; 977/777

(58) Field of Classification Search
USPC .................................. 502/243, 344; 977/777
See application file for complete search history.

(56) References Cited

U.S. PATENT DOCUMENTS

| | | | |
|---|---|---|---|
| 4,617,395 A | 10/1986 | Dockner et al. | |
| 5,700,942 A | 12/1997 | McAteer et al. | |
| 6,103,904 A | 8/2000 | Eva | |
| 7,371,457 B2 * | 5/2008 | Oldenburg et al. | 428/403 |
| 7,524,351 B2 * | 4/2009 | Hua et al. | 75/252 |
| 7,560,410 B2 * | 7/2009 | Pillai et al. | 502/304 |
| 7,629,291 B2 * | 12/2009 | Dai et al. | 502/344 |
| 2006/0293175 A1 * | 12/2006 | Dai et al. | 502/208 |
| 2008/0008639 A1 * | 1/2008 | Sakurai et al. | 423/230 |
| 2008/0206562 A1 * | 8/2008 | Stucky et al. | 428/403 |
| 2011/0053020 A1 * | 3/2011 | Norton et al. | 429/425 |
| 2011/0184206 A1 * | 7/2011 | Suzuki et al. | 560/103 |
| 2011/0244003 A1 * | 10/2011 | Kumaraswamy et al. | 424/400 |
| 2011/0250122 A1 * | 10/2011 | Joo et al. | 423/437.2 |
| 2011/0311635 A1 * | 12/2011 | Stucky et al. | 424/490 |

OTHER PUBLICATIONS

Chen et al., "Preparation and application of highly dispersed gold nanoparticles supported on silica for catalytic hydrogenation of aromatic nitro compounds", Journal of Catalysis 242 (2006) 227-230.*
Westcott et al., "Formation and Adsorption of Clusters of Gold Nanoparticles onto Funcationalized Silica Nanoparticle Surfaces", Langmuir 1998, 14, 5396-5401.*
Pol et al., "Deposition of Gold Nanoparticles on Silica Spheres: A Sonochemical Approach", Chem. Mater. 2003, 15, 1111-1118.*

(Continued)

*Primary Examiner* — Anthony J Zimmer
(74) *Attorney, Agent, or Firm* — Amin, Turocy & Watson, LLP

(57) ABSTRACT

Solid-supported gold nanoparticles for use as a catalyst for the synthesis of quinolines from anilines and aldehydes using oxygen as an oxidant are provided. Also provided are a method for the preparation of $SiO_2$-supported gold nanoparticles by in situ deposition of gold nanoparticles to silica gel and a method for synthesizing quinolines from anilines and aldehydes using oxygen as an oxidant.

8 Claims, 8 Drawing Sheets

(56) References Cited

OTHER PUBLICATIONS

Mukherjee et al., "Characterization and Catalytic Activity of Gold Nanoparticles Synthesized by Autoreduction of Aqueous Chloroaurate Ions with Fumed Silica", Chem. Mater. 2002, 14, 1678-1684.*

So et al., "Silica-Supported Gold Nanoparticles Catalyzed One-Pot, Tandem Aerobic Oxidative Cyclization Reaction for Nitrogen-Containing Polyheterocyclic Compounds", ChemCatChem 2011, 3, 386-393. Available Online Dec. 23, 2010.*

Okumura et al., "Preparation of supported gold catalysts by gas-phase grafting of gold acethylacetonate for low-temperature oxidation of CO and of H2," Journal of Molecular Catalysis A: Chemical 199 (2003) 73-84.*

Sylysia FCP Product Brochure. Fuji Silysia Chemical LTD. Printed Jun. 4, 2013.*

Lee, J.M., et al., "Cooperative multi-catalyst systems for one-pot organic transformations", Chem. Soc. Rev., 2004, 33, pp. 302-312.

Wasilke, Julia-Christina, et al., "Concurrent Tandem Catalysis", Chem. Rev., 2005, 105, pp. 1001-1020.

Shao, Z., et al., "Combining transition metal catalysis and organocatalysis: a broad new concept for catalysis", Chem. Soc. Rev., 2009, 38, pp. 2745-2755.

Wang, Congyang, et al., "Co-operative effect of Lewis acids with transition metals for organic synthesis", Chem. Soc. Rev., 2007,36, pp. 1395-1406.

Yu, Xingxin, et al., "Multicatalytic tandem reaction of N'-(2-alkynylbenzylidene) hydrazide with indole", Org. Biomol. Chem., 2009, 7, pp. 4526-4530.

Anastas, Paul, et al., "Origins, Current Status, and Future Challenges of Green Chemistry", Accounts of Chemical Research, 2002, 35, pp. 686-694.

Trost, Barry M., "On inventing reactions for atom economy", Accounts of Chemical Research, 2002, 35, pp. 695-705.

Felpin, F., et al., "Heterogeneous Multifunctional Catalysts for Tandem Processes: An Approach toward Sustainability", ChemSusChem, 2008, 1, pp. 718-724.

Zhu, Bolin, et al., "Aerobic oxidation of amines to imines catalyzed by bulk gold powder and by alumina-supported gold", Journal of Catalysis, 260, 2008, pp. 1-6.

So, Man-Ho, et al., "Graphite-Supported Gold Nanoparticles as Efficient Catalyst for Aerobic Oxidation of Benzylic Amines to Imines and N-Substituted 1,2,3,4-Tetrahydroisoquinolines to Amides: Synthetic Applications and Mechanistic Study", Chem. Asian J., 2009, 4, pp. 1551-1561.

Aschwanden, Linda, et al., "Magnetically Separable Gold Catalyst for the Aerobic Oxidation of Amines", ChemCatChem, 2009, 1, pp. 111-115.

Aschwanden, Linda, et al.,"A simple preparation of an efficient heterogeneous gold catalyst for aerobic amine oxidation", Journal of Molecular Catalysis A: Chemical 309 (2009) pp. 57-62.

Aschwanden, Linda, et al., "Development of a New Generation of Gold Catalysts for Amine Oxidation", ChemCatChem, Feb. 2010, pp. 666-673.

Carrettin, S., et al., "Nanocrystalline CeO Increases the Activity of Au for CO Oxidation by Two Orders of Magnitude", Angew. Chem. Int. Ed., 2004, 43, pp. 2538-2540.

Abad, Alberto, et al., "A Collaborative Effect between Gold and a Support Induces the Selective Oxidation of Alcohols", Angew. Chem. Int. Ed., 2005, 44, pp. 4066-4069.

Boronat, Merce, et al., "A Molecular Mechanism for the Chemoselective Hydrogenation of Substituted Nitroaromatics with Nanoparticles of Gold on TiO Catalysts: A Cooperative Effect between Gold and the Support", J Am. Chem. Soc., 2007, 129, pp. 16230-16237.

Corma, A., et al., "Supported gold nanoparticles as catalysts for organic reactions", Chem. Soc. Rev., 2008,37, pp. 2096-2126.

Rodriguez, J., et al., "Role of Au-C Interactions on the Catalytic Activity of Au Nanoparticles Supported on TiC(001) toward Molecular Oxygen Dissociation", J. Am. Chem. Soc., 2010, 132, pp. 3177-3186.

Florez, E., et al., "Effect of the Support on the Electronic Structure of Au Nanoparticles Supported on Transition Metal Carbines: Choice of the Best Substrate for Au Activation", J. Phys. Chem. C 2009, 113, pp. 19994-20001.

Santos, L., et al. "Chemoselective Synthesis of Substituted Imines, Secondary Amines, and B-Amino Carbonyl Compounds from Nitroaromatics through Cascade Reactions on Gold Catalysts", Chem. Eur. J, 2009, 15, pp. 8196-8203.

Biella, S., et al., "Gas phase oxidation of alcohols to aldehydes or ketones catalysed by supported gold", Chem. Commun., 2003, pp. 378-379.

Okumura, M., et al., "Preparation of supported gold catalysts by gas-phase grafting of gold acethylacetonate for low-temperature oxidation of CO and of H", Journal of Molecular Catalysis A:Chemical 199, 2003, pp. 73-84.

Zanella, R., et al., "New Preparation Method of Gold Nanoparticles on SiO", J. Phys. Chem. B, 2006, 110, pp. 8559-8565.

Yin, H., "Promotion of Au(en)Cl-Derived Au/Fumed SiO by Treatment with KMnO", J. Phys. Chem. C, 2008, 112, pp. 8349-8358.

Gaja, D., et al., "Gold Nanoparticles Supported on Passivated Silica:Access to an Efficient Aerobic Epoxidation Catalyst and the Intrinsic Oxidation Activity of Gold", J. Am. Chem. Soc. 2009, 131, pp. 14667-14669.

Igarashi, T., et al., "One-pot Synthesis of Substituted Quinolines by Iridium-catalysed Three-component Coupling Reaction", Chemistry Letters, vol. 34, No. 1 (2005) pp. 106-107.

Nakajima, T., et al., "Facile Three-Component Synthesis of Substituted Quinolines Catalyzed by Iridium(III) Complex", Bull. Chem, Soc. Jpn. vol. 79, No. 12, 2006, pp. 1941-1949.

Tanaka, S., "Practical and Simple Synthesis of Subsituted Quinolines by an HCl-DMSO system on a large scale: Remarkable Effect of the Chloride Ion", J. Org. Chem., 2006, 71, pp. 800-803.

Zhou, Y., "Catalytic Reactions of Carbene Precursors on Bulk Gold Metal", J. Am. Chem. Soc., 2009, 131, pp. 11734-11743.

Lowry, M., et al., "Accelerated Luminophore Discovery through Combinatorial Synthesis", J. Am. Chem. Soc., 2004, 126, pp. 14129-14135.

Williams, J.A. Gareth, "Photochemistry and Photophysics of Coordination Compounds: Platinum", Top Curr Chem, 2007, 281: 205-268.

Ghedini, M., et al., "Spectroscopy and electrochemical properties of a homologous series of acetylacetonato and hexafluoroacetylacetonato cyclopalladated and cycloplatinated complexes" The Royal Society of Chemistry, Dalton Trans, 2008, pp. 4303-4318.

Ulbricht, C., et al., et al., "Recent Developments in the Application of Phosphorescent Iridium(III) Complex Systems", Adv. Mater, 2009, 21, pp. 4418-4441.

Niknam, K., et al., "Molydatophosphoric Acid/Nallo/Wet SiO as an Efficient System for the Aromatization of 1,2- Dihydroquinolines under Mild and Heterogeneous Conditions", Synthetic Communications, 37, 2007, pp. 1091-1096.

Niknam, K., et al., "Silica sulfuric acid promoted aromatization of 1,2-Dihydroquinolines by using NaNO as oxidizing agent under mild and heterogeneous conditions", Catalysis Communications, 8, 2007 pp. 1427-1430.

de Fremont, Pierre, et al., "Synthesis and Structural Characterization of N-Heterocyclic Carbene Gold (I) Complexes", Organometallics, 2005, 24, pp. 2411-2418.

Kar-Yan, Vanessa, et al., "Gold(III) Salen Complex-Catalyzed Sythesis of Propargylamines via a Three-Component Coupling Reaction", Organic Letters, 2006, vol. 8, No. 8, pp. 1529-1532.

Che, Chi-Ming, et al., "Gold (III) porphyrins as a new class of anticancer drugs: cytotoxicity, DNA binding and induction of apoptosis in human cervix eptheloid cancer cells", Chem. Commun., 2003, pp. 1718-1719.

Wang, Ying, et al., "Gold (III) Porphyrin 1a Induced Apoptosis by Mitochondrial Death Pathways Related to Reactive Oxygen Species", Cancer Research, 2005, 65, pp. 11553-11564.

(56) References Cited

OTHER PUBLICATIONS

Li, Wei, et al., "A Selective Matrix Metalloprotease 12 Inhibitor for Potential Treatment of Chronic Obstructive Pulmonary Disease (COPD): Discovery of (S)-2-(8(Methoxycarbonylamino)dibenzo[b,d]furan-3-sulfonamido)-3-methylbutanoic acid (MMP408)", J. Med. Chem, 2009, 52, pp. 1799-1802.

So, Man-ho, et al., "Silica-Supported Gold Nanoparticles Catalyzed One-Pot Tandem Aerobic Oxidative Cyclization Reaction for Nitrogen-Containing Polyheterocyclic Compounds", ChemCatChem, 2010, 2, pp. 1-9.

Tanaka, Shin-ya, et al., "Practical and Simple Synthesis of Substituted Quinolines by an HCI-DMSO System on a Large Scale: Remarkable Effect of the Chloride Ion", J. Org. Chem., 2006, 71, pp. 800-803.

Nakajima, Takayuki, et al., "Facile Three-Component Synthesis of Substituted Quinolines Catalyzed by Iridium (III) Complex", Bull. Chem, Soc. Jpn., 2006, vol. 79, No. 12, pp. 1941-1949.

Manske, R. H., "The Chemistry of Quinolines", Chem. Rev., 1942, 30, pp. 113-144.

Igarashi, Takeyuki, et al., "One-pot Synthesis of Substituted Quinolines by Iridium-catalyzed Three-component Coupling Reaction", Chemistry Letters, vol. 34, No. 1, 2005, pp. 106-107.

* cited by examiner

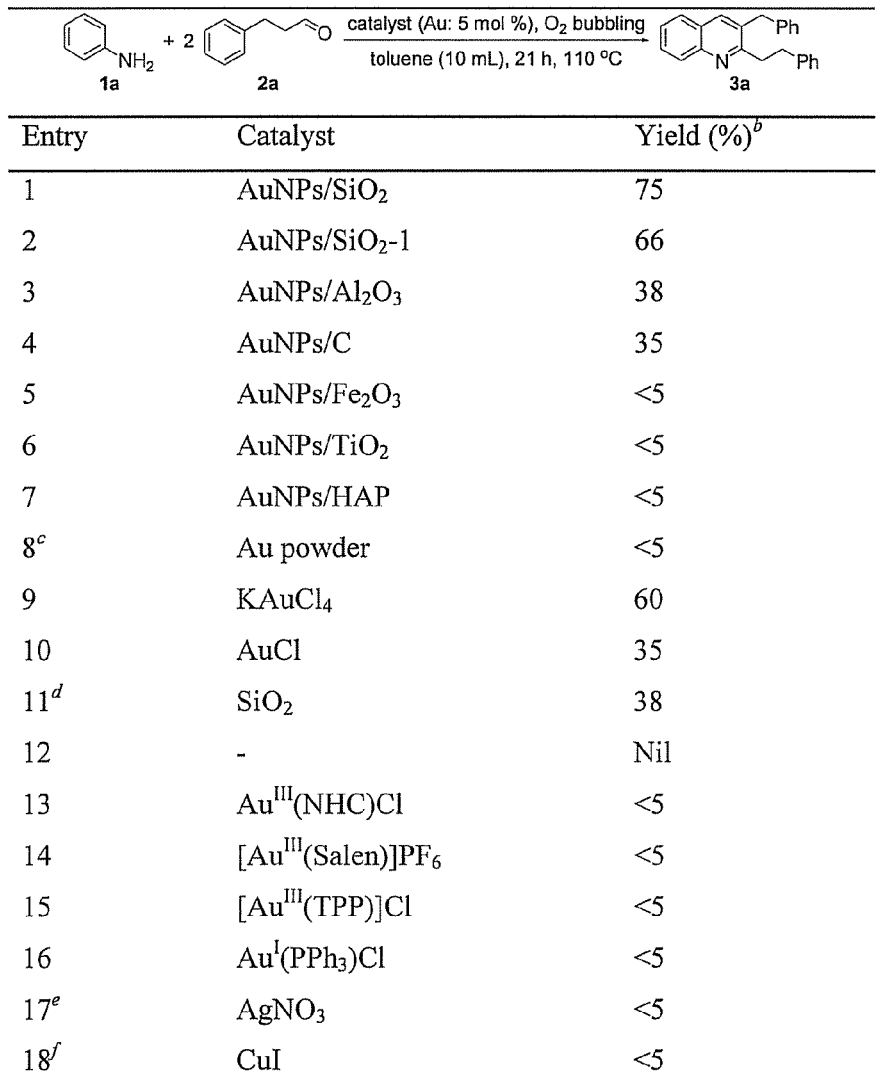

| Entry | Catalyst | Yield (%)[b] |
|---|---|---|
| 1 | AuNPs/SiO$_2$ | 75 |
| 2 | AuNPs/SiO$_2$-1 | 66 |
| 3 | AuNPs/Al$_2$O$_3$ | 38 |
| 4 | AuNPs/C | 35 |
| 5 | AuNPs/Fe$_2$O$_3$ | <5 |
| 6 | AuNPs/TiO$_2$ | <5 |
| 7 | AuNPs/HAP | <5 |
| 8[c] | Au powder | <5 |
| 9 | KAuCl$_4$ | 60 |
| 10 | AuCl | 35 |
| 11[d] | SiO$_2$ | 38 |
| 12 | - | Nil |
| 13 | Au$^{III}$(NHC)Cl | <5 |
| 14 | [Au$^{III}$(Salen)]PF$_6$ | <5 |
| 15 | [Au$^{III}$(TPP)]Cl | <5 |
| 16 | Au$^{I}$(PPh$_3$)Cl | <5 |
| 17[e] | AgNO$_3$ | <5 |
| 18[f] | CuI | <5 |

[a] Reaction conditions: 1a (0.2 mmol), 2a (0.5 mmol), catalyst (Au: 5 mol %), toluene (10 mL), O$_2$ bubbling, 110 °C, $t$ = 21 h, unless otherwise stated. [b] Yield was determined by $^1$H-NMR using Ph$_2$C=CH$_2$ as the internal standard and calculated based on the amount of 1a added. [c] Au powder (2.0 mg) was used. [d] Acid washed SiO$_2$ (100 mg) was used. [e] AgNO$_3$ (1.7 mg; Ag: 5 mol %) was used. [f] CuI (2.0 mg; Cu: 5 mol %) was used.

FIG. 5

| Entry | Catalyst | Run | Yield (%)[b] |
|---|---|---|---|
| 1 | AuNPs/SiO$_2$ | 1st | 75 |
| 2 | | 2nd | 75 |
| 3 | | 3rd | 78 |
| 4 | | 4th | 75 |
| 5 | | 5th | 71 |
| 6 | | 6th | 73 |
| 7 | | 7th | 73 |

[a] Reaction condition: 1a (0.2 mmol), 2a (0.5 mmol), AuNPs/SiO$_2$ (Au: 5 mol %), toluene (10 mL), O$_2$ bubbling, 110 °C, $t$ = 21 h, unless otherwise stated. [b] Yield was determined by $^1$H-NMR using Ph$_2$C=CH$_2$ as the internal standard and calculated based on the amount of 1a added.

FIG. 6

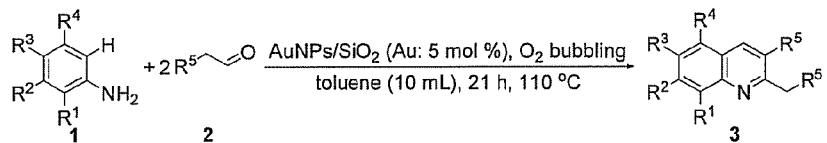

| Entry | Aniline | | | | | Aldehyde | | Product | Yield (%)[b] |
|---|---|---|---|---|---|---|---|---|---|
| | $R^1$ | $R^2$ | $R^3$ | $R^4$ | | $R^5$ | | | |
| 1 | H | H | H | H | 1a | PhCH$_2$ | 2a | 3a | 75 |
| 2 | H | H | i-Pr | H | 1b | PhCH$_2$ | 2a | 3b | 72 |
| 3 | H | H | Me | H | 1c | PhCH$_2$ | 2a | 3c | 66 |
| 4 | H | Me | H | H | 1d | PhCH$_2$ | 2a | 3d-7 & 3d-5 | 92[c] |
| 5 | Me | H | H | H | 1e | PhCH$_2$ | 2a | 3e | 66 |
| 6 | Me | H | H | Me | 1f | PhCH$_2$ | 2a | 3f | 65 |
| 7 | Me | H | Me | H | 1g | PhCH$_2$ | 2a | 3g | 70 |
| 8 | Me | Me | H | H | 1h | PhCH$_2$ | 2a | 3h | 82 |
| 9 | H | H | OMe | H | 1i | PhCH$_2$ | 2a | 3i | 45 |
| 10 | H | OMe | H | H | 1j | PhCH$_2$ | 2a | 3j-7 & 3j-5 | 83[d] |
| 11 | H | OMe | OMe | OMe | 1k | PhCH$_2$ | 2a | 3k | 95 |
| 12 | Ph | H | H | H | 1l | PhCH$_2$ | 2a | 3l | 82 |
| 13[e] | 1m | | | | | PhCH$_2$ | 2a | 3m | 60 |
| 14 | H | H | Cl | H | 1n | PhCH$_2$ | 2a | 3n | 17 |
| 15[f] | H | H | H | H | 1a | CH$_3$ | 2b | 3o | 54 |
| 16[f] | Me | Me | H | H | 1h | CH$_3$ | 2b | 3p | 64 |
| 17[f] | H | OMe | OMe | OMe | 1k | CH$_3$ | 2b | 3q | 81 |
| 18[f] | H | OMe | OMe | OMe | 1k | CH$_3$(CH$_2$)$_3$ | 2c | 3r | 91 |
| 19 | H | H | H | H | 1a | CH$_3$(CH$_2$)$_9$ | 2d | 3s | 71 |
| 20 | H | OMe | OMe | OMe | 1k | CH$_3$(CH$_2$)$_9$ | 2d | 3t | 92 |

[a] Reaction condition: 1 (0.2 mmol), 2 (0.5 mmol), AuNPs/SiO$_2$ (Au: 5 mol %), toluene (10 mL), O$_2$ bubbling, 110 °C, $t$ = 21 h; unless otherwise stated. [b] Yield was determined by $^1$H-NMR using Ph$_2$C=CH$_2$ as the internal standard and calculated based on the amount of 1 added. [c] The ratio of 7-isomer (3d-7) and 5-isomer (3d-5) was 6:1. [d] The ratio of 7-isomer (3j-7) and 5-isomer (3j-5) was 9:1. [e] 2a (1 mmol) and AuNPs/SiO$_2$ (Au: 10 mol %) was used. [f] 2 (1 mmol) was used. Reaction was performed under O$_2$ atmosphere (1 atm) instead of O$_2$ bubbling.

FIG. 7

| Entry | Polycyclic aniline | Aldehyde | Product | Yield (%)[b] |
|---|---|---|---|---|
| 1 | 4a | 2a | 5a | 85 |
| 2 | 4b | 2a | 5b | 93 |
| 3 | 4c | 2a | 5c | 96 |
| 4 | 4d | 2a | 5d | 80 |
| 5 | 4e | 2a | 5e | 82 |
| 6 | 4f | 2a | 5f | 82 |
| 7 | 4g | 2a | 5g | 65 |
| 8 | 4h | 2a | 5h-1 & 5h-2 | 82[c] |
| 9 | 4i | 2a | 5i | 62 |
| 10 | 4j | 2a | 5j | 83 |

[a] Reaction condition: 4 (0.2 mmol), 2a (0.5 mmol), AuNPs/SiO$_2$ (Au: 5 mol %), toluene (10 mL), O$_2$ bubbling, 110 °C, $t$ = 21 h; unless otherwise stated. [b] Yield was determined by $^1$H-NMR using Ph$_2$C=CH$_2$ as the internal standard and calculated based on the amount of 4 added. [c] The ratio of 5h-1 and 5h-2 was 2:1.

SOLID SUPPORTED GOLD NANOPARTICLES, METHODS OF USE THEREOF, AND METHODS FOR MAKING SAME

CROSS-REFERENCE TO RELATED APPLICATIONS

This application claims priority to provisional application Ser. No. 61/334,804 filed on May 14, 2010, the entire contents of which is incorporated herein by reference.

TECHNICAL FIELD

Described are improved catalysts of gold nanoparticles, methods for making such catalysts including silicon dioxide (silica) supported gold nanoparticles, methods for synthesizing quinolines using such nanoparticles, and methods for making silicon dioxide supported gold nanoparticles.

BACKGROUND

Quinolines are prevalent in natural product chemistry, and are important building blocks in organic synthesis, drug discovery and materials science. Owing to their importance, various named reactions are used, including Combes quinolines synthesis, Conrad-Limpach synthesis, Doebner-Miller reaction, Friedlander synthesis, Povarov reaction, Camps quinolines synthesis, Knorr quinolines synthesis and Gould-Jacobs reaction. However, most of these reactions involve strong acid, toxic chemicals (nitrobenzene and iodine) and high temperature reactions, even though they lead to low yields. Although the use of an iridium catalyst might circumvent this problem, this homogeneous catalyst is difficult to recover and recycle. The high cost of iridium metal might also detract from its use. Thus, there is an urgent need to develop a recyclable catalytic system, preferably that uses non-toxic reagents in the synthetic reactions.

U.S. Pat. No. 6,103,904 (Eva) discusses iodide and iodide salts (such as sodium and potassium iodide) to synthesize quinolones. These catalysts apepar to require high pressure and temperature and use of toxic oxidizing agents including nitroaromatics and arsenic compounds. U.S. Pat. No. 5,700,942 (McAteer) discusses a process for preparing quinoline bases using non-metal catalysts including amorphous silica-alumina or zeolite. The reactions occur in vapor phase, and appear to require high temperature (400 to 550° C.). U.S. Pat. No. 4,617,395 (Dockner) relates to preparation of quinolines, but requires high boiling mineral oil (b.p. above 150° C.), and use a non-metal organic acid as a catalyst. The aldehydes useful in the method appear limited to α, β-monosaturated aldehyde, and require stoichiometric amounts of an oxidant which may be toxic, such as nitrobenzene, arsenic pentoxide, or iron (II) chloride.

Other more recent approaches to quinoline synthesis have included iridium complexes T. Igarishi, et al., *Chem. Lett.* 2005, 34, 106-07; T. Nakajima, et al., *Bull. Chem. Soc.* Jan. 2006, 79, 1941-49), or acid catalyzed synthesis of anilines with aldehydes to quinolines (S.-Y. Taualea, *J. Org. Chem.* 2006, 71, 800-03.). For general reviews on the synthesis of quinolines see Li, J. J. (ed.), Name Reactions in Heterocyclic Chemistry, Wiley-Interscience, Hoboken, N.J., 2005, pp. 35-494; J. A. Joule K. Mills Heterocyclic Chemistry, Wiley-Blackwell Oxford, 2010, pp. 188-198. The foregoing references are incorporated herein by reference. M. Sainsbury, *Heterocyclic Chemistry*, Royal Soc. Chem., Cambridge 2001, pp. 43-50; R. F. Manske, *Chem. Rev.* 1942, 30, 113-14.

The foregoing methods involve strenuous reaction conditions, toxic reactants, low yields, environmentally unfriendly methods, catalysts, or reactants, or a combination of the foregoing.

SUMMARY

The disadvantages of prior techniques are effectively addressed by the disclosure herein. This disclosure aims to develop an environmentally friendly catalytic system to synthesize quinolines using nanotechnology and an application of metal nanoparticles as catalysts for organic transformations. Because of its high surface area and high density of active sites, metal nanoparticles exhibit superior catalytic activities compared with the corresponding bulk materials. Among various gold catalysts examined, AuNPs/$SiO_2$ is the most effective catalyst for the synthesis of quinolines from aniline and aldehydes. The oxidant used for this reaction is oxygen, which is cheap and do not produce waste. In addition, AuNPs/$SiO_2$ can be easily recycled by centrifugation, and reused for seven times without significant deterioration of yields and selectivities. The same system can be used to synthesize nitrogen containing polyheterocyclic compounds.

Described herein are solid-supported gold nanoparticles for use as a catalyst for the synthesis of quinolines from anilines and aldehydes using oxygen as an oxidant. Also provided herein is a new method for the preparation of $SiO_2$-supported gold nanoparticles by in situ deposition of gold nanoparticles to silica gel. Also provided herein is a method for synthesizing quinolines from anilines and aldehydes using oxygen as an oxidant.

Briefly, a composition of silica-supported gold nanoparticles as an efficient and recyclable catalyst for the synthesis of quinolines from anilines to aldehydes is provided. The catalyst composition can be easily prepared by the reaction of $KAuCl_4$ and 4-methoxybenzylamine in the presence of $SiO_2$ in a refluxing toluene solution. Recyclable silica-supported gold nanoparticles (27.9±3.0 nm) effectively catalyze the aerobic oxidation of anilines with aldehydes to quinolines with yields up to 96% (30 examples).

BRIEF DESCRIPTION OF THE FIGURES AND TABLES

Figure 1:
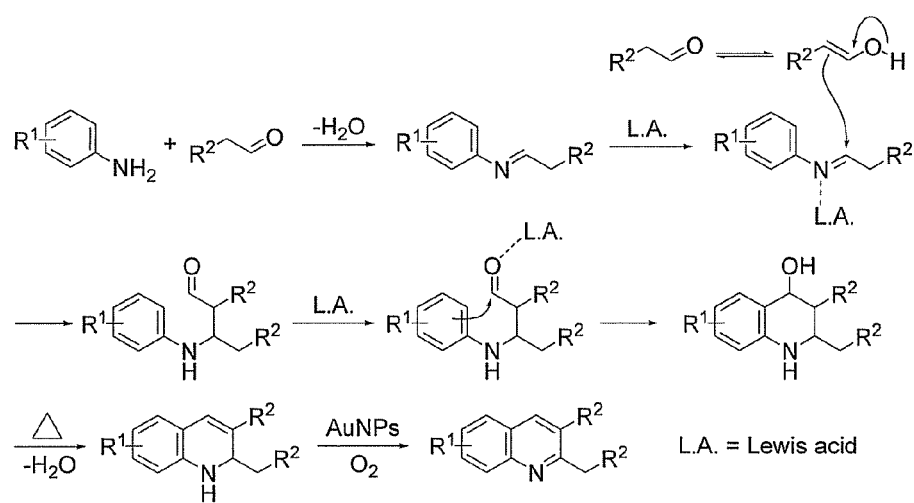
FIG. 1 illustrates the proposed mechanism for the oxidative cyclization reaction catalyzed by AuNPs/$SiO_2$.

FIG. 5 provides representative metal catalyst for the aerobic oxidative cyclization reaction.

FIG. 6 illustrates the recyclability of AuNPs/$SiO_2$ towards aerobic oxidative cyclization reaction.

FIG. 7 illustrates representative examples of quinolines by the used of "AuNPs/$SiO_2$+$O_2$" protocol.

FIG. 8 illustrates representative examples of nitrogen-containing polyheterocyclic compounds by the use of "AuNPs/$SiO_2$+$O_2$" protocol.

DETAILED DESCRIPTION

Commonly, gold nanoparticles (AuNPs) can be produced in a liquid by reduction of chloroauric acid ($HAuCl_4$), although other methods exist. After dissolving chloroauric acid, the solution is stirred while a reducing agent is added. This causes Au3+ ions to be reduced to form neutral gold atoms. As more and more of these gold atoms form, the solution becomes supersaturated, and gold gradually starts to precipitate in the form of sub-nanometer particles. The rest of the gold atoms that form stick to the existing particles, and, with increased levels of stirring, the particles have a fairly uniform size, while decreased levels of stirring provide with a range in size.

To prevent the particles from aggregating, an optional stabilizing agent can be added. The AuNPs can be functionalized with various organic ligands to create organic-inorganic hybrids with desired functionality.

The AuNPs have a size that facilitates the synthesis of quinolines. In one embodiment, AuNPs have an average size from 1 nm to 100 nm. In another embodiment, AuNPs have an average size from 5 nm to 75 nm. In yet another embodiment, AuNPs have an average size from 10 nm to 50 nm.

The AuNPs have a monodispersity in the silica that facilitates the synthesis of quinolines. In one embodiment, the AuNPs have a monodispersity in the silica from 1% to 40%. In another embodiment, the AuNPs have a monodispersity in the silica from 2% to 30%. In yet another embodiment, the AuNPs have a monodispersity in the silica from 5% to 20%.

Quinoline is a heterocyclic aromatic organic compound having the chemical formula $C_9H_7N$. For purposes herein, however, quinoline encompasses not only quinoline but also substituted and non-substituted quinolines, hydrogenated quinolines, dehydrogenated quinolines, quinoline analogs, polyquinolines, and the like.

Generally speaking, aniline and an aldehyde are reacted in the presence of a AuNPs/$SiO_2$ catalyst to form a quinoline. In a manner similar to the interpretation of quinoline, both aniline and aldehyde encompass substituted and non-substituted anilines and substituted and non-substituted aldehydes. Substituents for any of quinolines, anilines and/or aldehydes include alkyl groups, alkenyl groups, aromatic groups, aryl groups, heteroatom containing groups such as hydroxyl groups, alkoxy groups, hydroxylalky groups, amino groups, aminoalkyl groups, alkylamino groups, phenyl groups, and the like.

The substituents, when containing carbon, can contain from 1 to 18 carbon atoms. Any of the substituted quinolines, anilines and/or aldehydes can have one or more (such as two or more, three or more) substituents thereon.

Examples of aldehydes include formaldehyde, acetaldehyde, propionaldehyde, and butyraldehyde, although many others exist. Examples of substituted anilines include 2-methylaniline and N,N-dialkylanilines such as N,N-dimethylaniline.

An oxidant such as oxygen (or oxygen generating species) is provided to the aniline-aldehyde reaction to facilitate formation of the quinoline. Oxygen can simply be bubbled through the reaction mixture. The reaction takes place in any suitable solvent, such an organic solvent. The solvent is selected based on balancing the specific solubilities of the aniline, the aldehyde, and resultant quinoline. Examples of solvents include aromatic hydrocarbons such as benzene, toluene and xylene; halogenated hydrocarbons such as dichloromethane, chloroform, carbon tetrachloride, dichloroethane, chlorobenzene and dichlorobenzene; ethers such as diethyl ether, diisopropyl ether, tetrahydrofuran, dioxane, dimethoxyethane and diethyleneglycoldimethyl ether; amides such as formamide, N,N-dimethylformamide, N,N-dimethylacetamide, N-methyl-2-pyrrolidinone and hexamethylphosphorotriamide; or a solvent mixture of these can be mentioned.

The gold loading on $SiO_2$ is effective to facilitate the synthesis of quinolines. In one embodiment, the gold loading on silica is from 0.001 mmol/g to 100 mmol/g. In another embodiment, the gold loading on silica is from 0.01 mmol/g to 10 mmol/g. In another embodiment, the gold loading on silica is from 0.05 mmol/g to 1 mmol/g. Gold loading on silica can be determined by inductively coupled plasma-mass spectrometry (ICP-MS).

The AuNPs/$SiO_2$ catalyst has any size that facilitates the synthesis of quinolines. In one embodiment, the AuNPs/$SiO_2$ catalyst has an average particle size from 5 nm to 1 micron. In another embodiment, the AuNPs/$SiO_2$ catalyst has an average particle size from 10 nm to 0.5 micron. In yet another embodiment, the AuNPs/$SiO_2$ catalyst has an average particle size from 25 nm to 0.25 micron.

This disclosure relates to the use of $SiO_2$-supported gold nanoparticles (AuNPs/$SiO_2$) for the practical synthesis of quinolines. AuNPs/$SiO_2$ catalyst was prepared as follows: 4-methoxybenzylamine (1 mmol) was added into a refluxing toluene solution containing $KAuCl_4$ (0.1 mmol) and $SiO_2$ (1 g) and allowed to react for 6 h. The resulting solid was washed with piranha solution (30% $H_2O_2$/$H_2SO_4$=1/3 v/v) to remove residual organic substance capped onto the surface of AuNPs. After washing with water and centrifugation, AuNPs/$SiO_2$ particles were obtained as a brick red powder. The gold loading on $SiO_2$ was 0.1 mmol/g as revealed by inductively coupled plasma-mass spectrometry (ICP-MS). The presence of metallic gold on $SiO_2$ was confirmed by powder X-ray diffraction (XRD) (FIG. 1a), and the average diameter and monodispersity of the AuNPs were 27.7±2.9 nm and 11% respectively, as depicted from the transmission electron microscopy (TEM) image (FIG. 1b).

EXAMPLE 1

Catalytic Activity Screening

We screened the catalytic activities of various solid-supported AuNPs and gold salts towards the oxidative cyclization of 1a with 2a to give 3a using oxygen as an oxidant (Table 1). Among various gold catalysts, AuNPs/$SiO_2$ was the most active catalyst (entry 1). Similar product yield was found for AuNPs/$SiO_2$–1 catalyst prepared according to Rossi's method (entry 2).[3a] Low product yields of 3a were obtained when other solid-supported AuNPs catalysts were used (entries 3-7). Notably, reference catalysts from World Gold Council AuNPs/$Fe_2O_3$ (Sample No. 104C) and AuNPs/$TiO_2$ (Sample No. 168A) were inactive in this oxidative cyclization reaction (entries 5-6). Bulk gold powder (2-5 μm) was inactive under the employed reaction conditions (entry 8). $KAuCl_4$ and AuCl gave moderate yields of 3a (entries 9-10), but they could not be recycled. It should be noted that $SiO_2$ alone gave 3a in 38% yield accompanied with an equimolar amount of N-(3-phenylpropyl)benzenamine (formed by the reduction of imine) (entry 11), indicating that AuNPs plays a key role in catalyzing the aerobic oxidation. No product was found in the absence of gold catalyst (entry 12).

Figure 2:
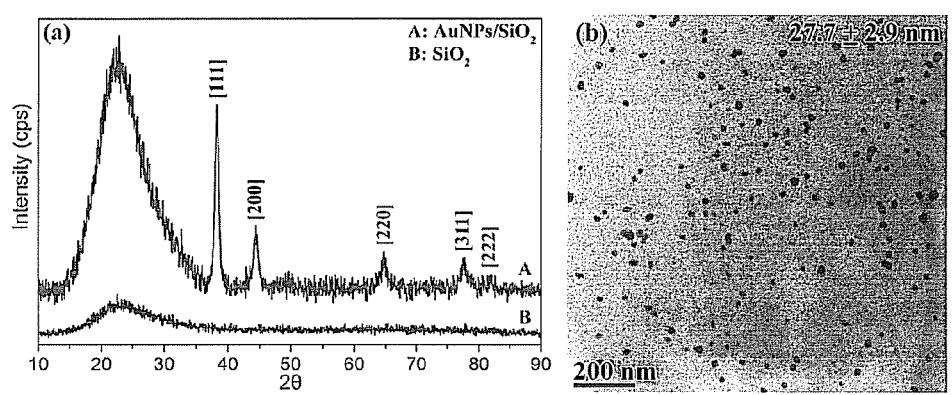
FIG. 2 shows (a) powder XRD pattern and (b) TEM image of AuNPs/$SiO_2$.

The organometallic gold complexes were also examined, but they showed no catalytic activities towards the oxidative cyclization reaction (entries 13-16). The chemical structures of these organometallic gold complexes are shown in FIG. 2. Other coinage group metal salts such as $AgNO_3$ and CuI were found to be catalytically inactive (entries 17-18).

EXAMPLE 2

Recycling Experiment

Figure 3:
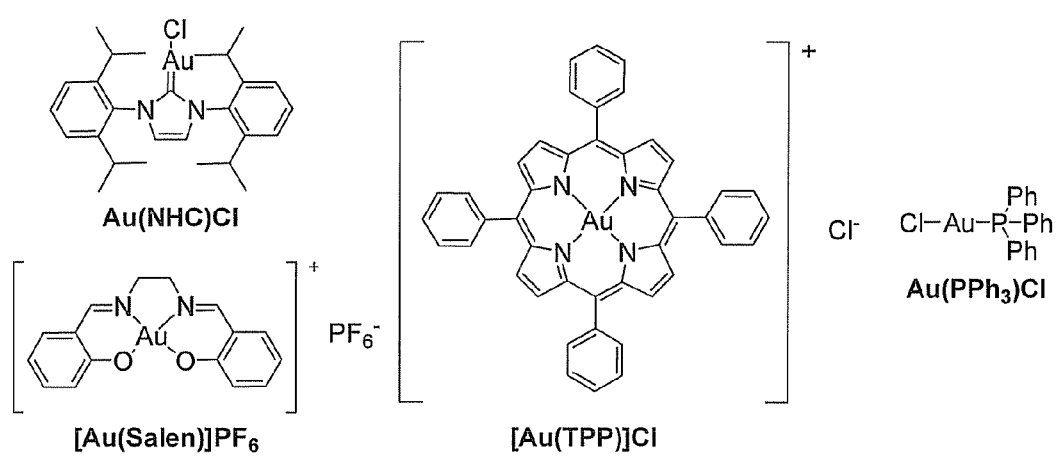
FIG. 3 shows the chemical structures of Au(NHC)Cl, [Au (Salen)]$PF_6$, [Au(TPP)]Cl and Au($PPh_3$)Cl complexes.
Figure 4:
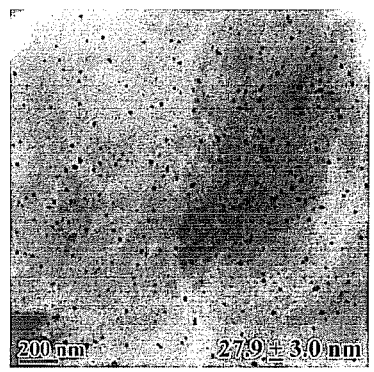
FIG. 4 shows a typical TEM image of AuNPs/$SiO_2$ after the seventh recycling run.

AuNPs/$SiO_2$ can be recovered by centrifugation and reused for seven consecutive runs without a significant loss of reactivity (Table 2). No significant change of the average particle size and monodispersity of the AuNPs were noted after each consecutive run. The average particle size and monodispersity of the AuNPs on SiO$_2$ after the seventh run were 27.9±3.0 nm and 10.8% respectively (FIG. 3). It is necessary to rinse the recovered AuNPs/SiO$_2$ catalyst with piranha solution before each recycling. Presumably, acid treatment can remove the organic impurity capped onto the surface of AuNPs and regenerate the active Au$^{\delta+}$ sites. Indeed, X-ray photoelectron spectroscopy (XPS) analysis revealed that there was an increase of binding energy from 83.9 eV to 84.4 eV (Au 4f$_{7/2}$) after the acid treatment, indicating a higher portion of Au$^{\delta+}$ species on the surface of the AuNPs.

EXAMPLE 3

Synthesis of Substituted Quinolines

Next, we examined the substrate scope of the "AuNPs/SiO$_2$+O$_2$" protocol. As depicted in Table 3, this protocol could effectively catalyze the cyclization of a variety of substituted anilines 1a-n with 2a to give 3a-n with product yields up to 95% (entries 1-14). Good to excellent product yields were obtained when anilines with electron-donating substituent were used (entries 1-13). Cyclization of o-tolidine 1m, which contains two aniline groups, gave the corresponding di-quinoline 3m with moderate yield (entry 13). Anilines with electron-donating substituent (CH$_3$ or OCH$_3$) at the meta-position gave better product yields than that of ortho- or para-substituted anilines (compare entries 4 and 10 with entries 3, 5 and 9). In containing an electron-deficient group gave poor product yield (entry 14). The oxidative cyclization of 1d or 1j with 2a both gave a mixture of 7- and 5-isomers in the ratios of 6:1 (3d-7:3d-5) and 9:1 (3j-7:3j-5) respectively, and similar selectivities have been reported in the related Ir-catalyzed reactions.[13b]

Apart from 2a, alkyl aldehydes 2b-d could also be used as the substrates (Table 3, entries 15-20). Relatively lower product yields of quinolines 3o-q are attributed to evaporation of the low boiling propanal 2b (46-50° C.) in the course of the reaction at 110° C. (entries 15-17). With high boiling aldehyde (2c-d), corresponding quinolines 3r-t were obtained in better yields (entry 18-20).

EXAMPLE 4

Synthesis of Nitrogen-Containing Polyheterocyclic Compounds

The "AuNPs/SiO$_2$+O$_2$" protocol is also applicable to the synthesis of nitrogen-containing polyheterocyclic compounds 5a-j using polycyclic anilines 4a-j with good to excellent product yields (Table 4). This protocol is effective even with bulky aniline 4j, resulting in polyheterocyclic compound 5j having five fused rings in 83% yield (entry 10). All of these results suggest that the "AuNPs/SiO$_2$+O$_2$" protocol is competent for preparing nitrogen-containing polyheterocyclic compounds, which can be used as chelating ligands for the design of cyclometalated transition metal complexes with novel materials and light emitting properties.

EXAMPLE 5

Mechanistic Studies

To get insight into the reaction mechanism, a radical trap experiment was performed. Addition of the radical scavenger 2,6-di-tert-butyl-4-methylphenol (5 equiv. to aniline 1a) to the reaction mixture did not significantly affect the yield of 3a (73% yield). We propose that the mechanism of the oxidative cyclization is a Lewis acid-catalyzed reaction through initial imine condensation and Mannich reaction, similar to the previous reports by Shimizu,[13b] and Baba,[13c] using [IrCl$_2$H (cod)]$_2$ and "HCl+DMSO" as catalyst (Scheme 1). The AuNPs/SiO$_2$ functions as a Lewis acid catalyst for the cyclization, while the AuNPs can catalyze the aerobic oxidation of 1,2-dihydroquinoline to 3.

EXAMPLE 6

Instrumental Analysis

In addition to electron microscopy and x-ray diffraction study, we have characterized the AuNPs/SiO$_2$ by x-ray photoelectron spectroscopy (XPS), selected area electron diffraction (SAED) and energy-dispersive X-ray microanalysis. Especially, XPS analysis of the AuNPs/SiO$_2$ catalyst showed a binding energy of 84.4 eV, revealing a higher portion of Au$^{\delta+}$ species on the surface of the AuNPs. The binding energy of bulk gold metal is 84.0 eV [Handbook of X-ray Photoelectron Spectroscopy (Eds.: J. Chastain, R. C. King), Physical Electronic, Eden Prairie, Minn. (1995). Both XRD and SEAD analyses strongly indicated that metallic gold particles were grafted on the SiO$_2$ surface. The gold loading on SiO$_2$ was 0.1 mmol/g as determined by inductively coupled plasma-mass spectrometry (ICP-MS).

With respect to any figure or numerical range for a given characteristic, a figure or a parameter from one range may be combined with another figure or a parameter from a different range for the same characteristic to generate a numerical range.

Other than in the operating examples, or where otherwise indicated, all numbers, values and/or expressions referring to quantities of ingredients, reaction conditions, etc., used in the specification and claims are to be understood as modified in all instances by the term "about."

The embodiments as disclosed and described in the application are intended to be illustrative and explanatory, and not limiting. Modifications and variations of the disclosed embodiments, for example, of the processes and apparatuses employed (or to be employed) as well as of the compositions and treatments used (or to be used), are possible; all such modifications and variations are intended to be within the scope of this application.

What is claimed is:

1. A catalyst composition, comprising:
   gold nanoparticles on a silica gel support, wherein gold loading on silica gel is from 0.001 mmol/g to 100 mmol/g; and
   the gold nanoparticles have a monodispersity in the silica gel from 1% to 40%.

2. A catalyst composition according to claim 1, wherein the gold nanoparticles have an average size from about 1 nm to 100 nm.

3. A catalyst composition according to claim 1, wherein the gold nanoparticles have an average size from about 5 nm to 75 nm.

4. A catalyst composition according to claim 1, wherein the gold loading on silica gel is from 0.01 mmol/g to 10 mmol/g.

5. A catalyst composition according to claim 1, wherein the gold nanoparticles have a monodispersity in the silica gel from 2% to 30%.

6. A catalyst composition according to claim 1, wherein the gold nanoparticles have a monodispersity in the silica gel from 5% to 20%.

7. A catalyst composition according to claim 1, further having an average particle size from 5 nm to 1 micron.

8. A catalyst composition according to claim 1, further having an average particle size from 10 nm to 0.5 micron.

\* \* \* \* \*